(12) United States Patent
Drucks et al.

(10) Patent No.: US 7,592,019 B2
(45) Date of Patent: Sep. 22, 2009

(54) COSMETIC OR DERMATOLOGICAL IMPREGNATED WIPES

(75) Inventors: Anja Drucks, Hamburg (DE); Stephanie von der Fecht, Schenefeld (DE); Jörg Küther, Schenefeld (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/001,565

(22) Filed: Nov. 15, 2001

(65) Prior Publication Data

US 2002/0102289 A1 Aug. 1, 2002

(30) Foreign Application Priority Data

Nov. 30, 2000 (DE) ................ 100 59 584

(51) Int. Cl.
*A61K 8/02* (2006.01)
*A61K 9/70* (2006.01)
*A61K 36/00* (2006.01)
*A61K 8/18* (2006.01)
*B32B 27/04* (2006.01)

(52) U.S. Cl. .................. 424/443; 424/59; 424/725; 442/123

(58) Field of Classification Search .......... 424/443, 424/447, 424, 487; 428/289, 224; 514/844–848, 514/853–865

See application file for complete search history.

(56) References Cited

U.S. PATENT DOCUMENTS

| 2,862,251 A | 12/1958 | Kalwaites |
|---|---|---|
| 3,485,706 A | 12/1969 | Evans |
| 3,494,821 A | 2/1970 | Evans |
| 4,818,594 A * | 4/1989 | Albien et al. ............... 442/121 |
| 4,902,564 A | 2/1990 | Israel et al. |
| 5,043,155 A | 8/1991 | Puchalski et al. |
| 5,635,191 A | 6/1997 | Roe et al. |
| 5,674,591 A | 10/1997 | James et al. |
| 5,863,663 A | 1/1999 | Mackey et al. |
| 5,871,762 A | 2/1999 | Venkitaraman et al. |
| 5,879,666 A | 3/1999 | Lucas et al. |
| 5,952,043 A | 9/1999 | Mackey et al. |
| 6,245,322 B1 * | 6/2001 | Simon .......................... 424/59 |
| 6,361,784 B1 * | 3/2002 | Brennan et al. .............. 424/402 |
| 2002/0071859 A1 * | 6/2002 | Gott et al. .................... 424/443 |
| 2002/0160681 A1 | 10/2002 | Noelle |

FOREIGN PATENT DOCUMENTS

| DE | 40 00 920 A1 | 7/1991 |
|---|---|---|
| DE | 42 04 222 C1 | 4/1993 |
| DE | 296 12 828 U1 | 11/1996 |
| DE | 19715385 | 10/1998 |
| DE | 19903903 | 8/2000 |
| DE | 299 04 320 U1 | 10/2000 |
| EP | 0483816 | 5/1992 |
| EP | 0613675 | 9/1994 |
| EP | 0750063 | 12/1996 |
| EP | 0 652 988 B1 | 4/1998 |
| EP | 0 792 144 B1 | 12/1998 |
| EP | 1046747 | 10/2000 |
| GB | 2328451 | 2/1999 |
| WO | 94/02674 | 2/1994 |
| WO | 96/24329 | 8/1996 |
| WO | 98/34781 | 8/1998 |
| WO | 99/07273 | 2/1999 |
| WO | 99/25318 | 5/1999 |
| WO | 01/25522 | 4/2001 |

OTHER PUBLICATIONS

English language Abstract of DE 199 03 903.
English language Abstract of DE 19715385.
E. Fahrbach et al.: "Nonwoven Fabrics." in: Ullmann's Encyclopedia of Industrial Chemistry, vol. A17, Fifth revised edition, Wiley-VCH, 1999, pp. 565-587.
Papier-Lexikon, vol. 1, Eds: L. Göttsching, C. Katz, Deutscher Betriebswirte-Verlag GmbH, Gernsbach 1999, pp. 276-278.
ASTM Standard D5729-97, 1997.
EDANA Test Method: "Nonwovens Thickness", 30.5-99, Feb. 1999, pp. 1-6.

\* cited by examiner

*Primary Examiner*—Jennifer Myong M Kim
(74) *Attorney, Agent, or Firm*—Greenblum & Bernstein P.L.C.

(57) ABSTRACT

Cosmetic and dermatological wipes, where the wipes consist of a water-jet-consolidated and/or water-jet-impressed nonwoven material, which have been moistened with cosmetic and dermatological impregnation solutions which have a viscosity of less than 2000 mPa·s.

18 Claims, No Drawings

COSMETIC OR DERMATOLOGICAL IMPREGNATED WIPES

The present invention relates to surface-structured cosmetic and dermatological wipes which have been moistened with low-viscosity cosmetic and dermatological impregnation solutions. In particular, the invention relates to cosmetic and dermatological impregnated care, cleansing and deodorizing wipes, and to impregnated wipes for controlling skin diseases (such as acne etc.) and those which care for the skin in a targeted manner following sunburn and reduce the secondary reactions of the skin to the effect of UV radiation.

Impregnated wipes are used widely in very diverse areas as articles of everyday use. They permit, inter alia, efficient and mild cleansing and care, particularly also in the absence of (running) water.

In this connection, the actual article of use consists of two components:
a) a dry wipe constructed from materials such as paper and/or a very wide variety of mixtures of natural or synthetic fibers and
b) a low-viscosity impregnation solution.

Surface-structured wipes are also known per se. They are prepared on the basis of cellulose and are used in particular as household wipes and for perianal cleaning. Their structure is produced by mechanical impression by means of calender rolls. Such wipes have low tear resistance coupled with high roughness and hardness. They are therefore only of limited suitability for use on the human skin.

An object of the present invention was to find cosmetic or dermatological impregnated wipes which do not have the disadvantages of the prior art and are suitable in particular for the care and/or cleansing of the skin.

It was surprising and could not have been forseen by the person skilled in the art that cosmetic and dermatological wipes, where the wipes consist of water-jet-consolidated and/or water-jet-impressed nonwoven material, which have been moistened with cosmetic and dermatological impregnation solutions which have a viscosity of less than 2000 mPa·s, overcome the disadvantages of the prior art.

The wipes according to the invention represent the combination of a soft, water-insoluble nonwoven material which has a new type of structure with low-viscosity cosmetic and dermatological impregnation solutions. They are entirely satisfactory from any viewpoint and are accordingly very particularly suitable for serving as a basis for preparation forms with diverse applications. The wipes according to the invention exhibit very good sensory and cosmetic properties and are also distinguished by excellent skincare data.

The nonwoven material is preferably consolidated as spun lace material in the preparation process by water jets. The structuring then advantageously likewise takes place by means of water jets. This structuring produces a uniform sequence of elevations and indentations in the material. In combination with suitable impregnation solutions, this structuring permits, as a result of its elevations, both better access to indentations in the human skin and also, as a result of its structural values, increased soil-uptake capacity. This leads overall to a significantly improved cleaning performance.

In addition, better access to indentations in the human skin is of particular importance for controlling skin diseases and skin irritations and for effectively displaying a deodorizing action.

The cosmetic and dermatological impregnation solutions with which the wipes according to the invention have been moistened can be in various forms. They are preferably low-viscosity, in particular sprayable and have e.g. a viscosity of less than 2000 mPas, in particular, less than 1500 mPa·s (measuring instrument: Haake Viskotester VT-02 at 25° C.).

For the purposes of the present invention, the impregnation solutions can additionally comprise one or more water phases in addition to one or more oil phases and, for example, are in the form of W/O, O/W, W/O/W or O/W/O emulsions. Such formulations can preferably also be a microemulsion, a Pickering emulsion, a sprayable emulsion or a hydrodispersion.

Moreover, the formulations according to the invention can, however, also advantageously be in the form of oil-free preparations—such as, for example, as gels or (aqueous, alcoholic, aqueous-alcoholic) solutions.

For the purposes of the present invention, if the impregnation solution is a solution or dispersion, solvents which can be used are:
water or aqueous solution
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water may be a further constituent.

If the impregnation solution comprises one or more water phases, these may advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and polymers, foam stabilizers, electrolytes, sugar derivatives and/or moisturizers.

Moisturizers is the term used to describe substances or mixtures of substances which, following application or distribution on the surface of the skin, confer on cosmetic or dermatological preparations the property of reducing the moisture loss by the horny layer (also called transepidermal water loss (TEWL)) and/or have a beneficial effect on the hydration of the horny layer.

Advantageous moisturizers for the purposes of the present invention are, for example, glycerol, lactic acid, pyrrolidonecarboxylic acid and urea. In addition, it is particularly advantageous to use polymeric moisturizers from the group of polysaccharides which are soluble in water and/or swellable in water and/or gellable using water. Particularly advantageous are, for example, hyaluronic acid, chitosan and/or a fucose-rich polysaccharide which is listed in Chemical Abstracts under the registry number 178463-23-5 and is available, for example, under the name Fucogel®1000 from SOLABIA S.A.

Also advantageous for the purposes of the present invention are anhydrous preparations which, in addition to one or more oil components, can comprise further oil-soluble auxiliaries, additives and/or active ingredients.

If the impregnation solution comprises one or more oil phases, the oil(s) is/are advantageously chosen for the purposes of the present invention from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/ or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the oils can advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24, in particular 12 to 18 carbon atoms. The fatty acid triglycerides can, for example, advantageously be chosen from the group of synthetic, semisynthetic and natural oils, e.g. olive oil, sunflower oil, soybean oil, peanut oil, rapeseed oil, almond oil, palm oil, coconut oil, palm kernel oil and the like.

Any mixtures of such oil and wax components can also advantageously be used for the purposes of the present invention.

The oils are advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Particularly advantageous mixtures are those of $C_{12-15}$-alkyl benzoate and 2-ethylhexyl isostearate, those of $C_{12-15}$-alkyl benzoate and isotridecyl isononanoate, and those of $C_{12-15}$-alkyl benzoate, 2-ethylhexyl isostearate and isotridecyl isononanoate.

Of the hydrocarbons, paraffin oil, squalane and squalene are advantageously to be used for the purposes of the present invention.

The oil phase can advantageously further have a content of cyclic or linear silicone oils or consist entirely of such oils, as a result of which W/S (water-in-silicone), S/W (silicone-in-water) formulations, for example, and the like arise. However, apart from the silicone oil or the silicone oils, it is preferred to use an additional content of other oil phase components.

Cyclomethicone (octamethylcyclotetrasiloxane) is advantageously used as silicone oil to be used according to the invention. However, other silicone oils can also advantageously be used for the purposes of the present invention, for example hexamethylcyclotrisiloxane, polydimethylsiloxane, poly(methylphenylsiloxane).

Also particularly advantageous are mixtures of cyclomethicone and isotridecyl isononanoate, and of cyclomethicone and 2-ethylhexyl isostearate.

The oil(s) is/are also advantageously chosen from the group of phospholipids. The phospholipids are phosphoric esters of acylated glycerol. The most significant phosphatidylcholines are, for example, the lecithins, which are distinguished by the general structure

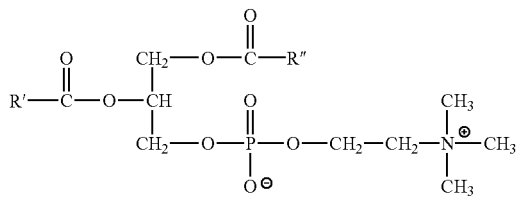

where R' and R'' are typically unbranched aliphatic radicals having 15 or 17 carbon atoms and up to 4 cis double bonds.

For the purposes of the present invention, the wipes advantageously comprise one or more washing-active surfactants from the following four groups A to D, in particular if they are to be used as cleansing wipes:

A. Anionic Surfactants

Anionic surfactants to be used advantageously are acylamino acids (and salts thereof), such as
1. acylglutamates, for example sodium acylglutamate, di-TEA-palmitoyl aspartate and sodium caprylic/capric glutamate,
2. acylpeptides, for example palmitoyl hydrolyzed milk protein, sodium cocoyl hydrolyzed soya protein and sodium/potassium cocoyl hydrolyzed collagen,
3. sarcosinates, for example myristoyl sarcosinate, TEA-lauroyl sarcosinate, sodium lauroyl sarcosinate and sodium cocoyl sarcosinate,
4. taurates, for example sodium lauroyl taurate and sodium methyl cocoyl taurate, carboxylic acids and derivatives, such as
1. carboxylic acids, for example lauric acid, aluminum stearate, magnesium alkanolate and zinc undecylenate,
2. ester carboxylic acids, for example calcium stearoyl lactylate, laureth-6 citrate and sodium PEG-4 lauramide carboxylate,
3. ether carboxylic acids, for example sodium laureth-13 carboxylate and sodium PEG-6 cocamide carboxylate, phosphoric acid esters and salts, such as, for example, DEA-oleth-10 phosphate and dilaureth-4 phosphate, sulfonic acids and salts, such as
1. acyl isethionates, e.g. sodium/ammonium cocoyl isethionate,
2. alkylarylsulfonates,
3. alkylsulfonates, for example sodium cocosmonoglyceride sulfate, sodium $C_{12-14}$-olefinsulfonate, sodium lauryl sulfoacetate and magnesium PEG-3 cocamide sulfate,
4. sulfosuccinates, for example dioctyl sodium sulfosuccinate, disodium laureth sulfosuccinate, disodium lauryl sulfosuccinate and disodium undecylenamido-MEA sulfosuccinate and sulfuric esters, such as
1. alkyl ether sulfates, for example sodium, ammonium, magnesium, MIPA, TIPA laureth sulfate, sodium myreth sulfate and sodium $C_{12-13}$ pareth sulfate,
2. alkyl sulfates, for example sodium, ammonium and TEA laurylsulfate.

B. Cationic Surfactants

Cationic surfactants to be used advantageously are
1. alkylamines,
2. alkylimidazoles,
3. ethoxylated amines and
4. quarternary surfactants.

Quaternary surfactants contain at least one N atom which is bonded covalently to 4 alkyl or aryl groups. Irrespective of the pH, this leads to a positive charge. Benzalkonium chloride, alkylbetaine, alkylamidopropylbetaine and alkylamidopropylhydroxysultaine are advantageous.

C. Amphoteric Surfactants

Amphoteric surfactants to be used advantageously are
1. acyl/dialkylethylenediamine, for example sodium acylamphoacetate, disodium acylamphodipropionate, disodium alkylamphodiacetate, sodium acylamphohydroxypropyl-sulfonate, disodium acylamphodiacetate and sodium acylamphopropionate,
2. N-alkylamino acids, for example aminopropylalkylglutamide, alkylaminopropionic acid, sodium alkylimidodipropionate and lauroamphocarboxyglycinate.

D. Nonionic Surfactants

Nonionic surfactants to be used advantageously are
1. alcohols,
2. alkanolamides, such as cocoamides MEA/DEA/MIPA,
3. amine oxides, such as cocamidopropylamine oxide,
4. esters which are formed by esterification of carboxylic acids with ethylene oxide, glycerol, sorbitol or other alcohols,
5. ethers, for example ethoxylated alcohols, ethoxylated lanolin, ethoxylated polysiloxanes, propoxylated POE ethers and alkyl polyglycosides, such as lauryl glycoside, decyl glycoside and cocoglycoside.

The impregnation solutions particularly advantageously comprise one or more washing-active surfactants from the group of surfactants which have an HLB value of more than 25, very particularly those which have an HLB value of more than 35.

For the purposes of the present invention, it is advantageous if the content of one or more washing-active surfactants in the cosmetic or dermatological impregnation solution is chosen from the range from 5 to 25% by weight, very particularly advantageously from 10 to 15% by weight, in each case based on the total weight of the impregnation solution.

Furthermore, the impregnation solutions for the cosmetic and dermatological wipes according to the invention also advantageously comprise preservatives.

Preservatives are antimicrobial substances which are added during the preparation process to a product (foods or confectionery, pharmaceutical, cosmetic or also chemicotechnical preparations) in small amounts (usually between about 0.0005% and 1% active content, depending on the product). Preservatives are intended to protect products during preparation, storage and use against contamination by microorganisms, in particular against detrimental changes caused microbially.

A preservative is, in principle, subject to the following requirements: it must be sufficiently antimicrobially effective, technologically applicable and safe with regard to health. The aspect of safety with regard to health must, however, also be satisfied by the finished preparation, the commercial product. In this connection, it is to be taken into consideration that microorganisms may be present in e.g. cosmetic products primarily as a result of production, or may secondarily be passed into the cosmetic product by the consumer.

For this reason, it must be ensured that the finished product is also safe over the entire use period.

Most preservatives intended or proposed for preservation have a bacteriostatic and fungistatic action, sometimes also a bactericidal and fungicidal action: they should be odorless and tasteless and, in the doses used, as far as possible be soluble, nontoxic, skin-compatible and sufficiently effective. The preservatives must, in order to be effective, be dissolved in the crude material or auxiliary to be preserved. Since most preservatives are more soluble in fat than water, it must be taken into account that e.g. in an emulsion whose aqueous phase is to be preserved, the preservative incorporated into the aqueous phase migrates into the fatty phase over the course of storage, thus jeopardizing preservation of the aqueous phase. For this reason, it is advisable to use a combination of preservatives, i.e. to preserve the aqueous phase with a preservative which is readily soluble in water, but at the same time to preserve the fatty phase with a preservative which is soluble in fat.

Although sterility is not generally required for a cosmetic preparation, it must, however, be free from pathogenic microbes and be protected from changes caused microbially.

It should be taken into consideration that different types of emulsion, aqueous solutions, suspensions etc. require different preservation, that the preserving action of individual preservatives is dependent on the composition and the physical properties of the preparation to be preserved, that interactions between the preservative, the active ingredients and auxiliaries are to be taken into account, that various active ingredients or auxiliaries can adsorb preservatives and thus possibly deactivate them, that, in particular, hydrocolloids present in the preparation may, depending on the concentration, hinder the the antimicrobial activity of preservatives and that, finally, again depending on the concentration and the type of preservative, the stratum corneum adsorbs the preservative, this then possibly leading to permeation and absorption of the preservative.

Preservatives permitted in food technology which can also be advantageously used for the purposes of the present invention are listed below with their E numbers.

| E 200 | Sorbic acid | E 227 | Calcium hydrogensulfite |
|---|---|---|---|
| E 201 | Sodium sorbate | E 228 | Potassium hydrogensulfite |
| E 202 | Potassium sorbate | E 230 | Biphenyl (diphenyl) |
| E 203 | Calcium sorbate | E 231 | Orthophenylphenol |
| E 210 | Benzoic acid | E 232 | Sodium orthophenylphenoxide |
| E 211 | Sodium benzoate | E 233 | Thiabendazole |
| E 212 | Potassium benzoate | E 235 | Natamycin |
| E 213 | Calcium benzoate | E 236 | Formic acid |
| E 214 | p-Hydroxybenzoic ethyl ester | E 237 | Sodium formate |
| E 215 | p-Hydroxybenzoic ethyl ester Na salt | E 238 | Calcium formate |
| E 216 | p-Hydroxybenzoic n-propyl ester | E 239 | Hexamethylenetetramine |
| E 217 | -Hydroxybenzoic n-propyl ester Na salt | E 249 | Potassium nitrite |
| E 218 | p-Hydroxybenzoic methyl ester | E 250 | Sodium nitrite |
| E 219 | p-Hydroxybenzoic methyl ester Na salt | E 251 | Sodium nitrate |
| E 220 | Sulfur dioxide | E 252 | Potassium nitrate |
| E 221 | Sodium sulfite | E 280 | Propionic acid |
| E 222 | Sodium hydrogensulfite | E 281 | Sodium propionate |
| E 223 | Sodium disulfite | E 282 | Calcium propionate |
| E 224 | Potassium disulfite | E 283 | Potassium propionate |
| E 226 | Calcium sulfite | E 290 | Carbon dioxide |

Also advantageous are preservatives or preservative auxiliaries customary in cosmetics, such as dibromodicyanobutane (2-bromo-2-bromomethylglutarodinitrile), phenoxyethanol, 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol.

For the purposes of the present invention, particularly advantageous cosmetic impregnation solutions further comprise antioxidants as additives or active ingredients. According to the invention, the preparations advantageously comprise one or more antioxidants. Favorable, but nevertheless optional antioxidants which may be used are all antioxidants customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocaninic acid) and derivatives thereof, peptides such as D, L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and conyferyl benzoate of benzoin resin, rutinic acid and derivatives thereof, ferulic acid and derivatives thereof, butylhydroxy toluene, butylhydroxy anisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these active ingredients which are suitable according to the invention.

For the purposes of the present invention, water-soluble antioxidants can be used particularly advantageously.

Preferred active ingredients are antioxidants which are able to protect the skin from oxidative stress. Particularly preferred antioxidants here are vitamin E and derivatives thereof, and vitamin A and derivatives thereof.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant(s), it is advantageous to choose their respective concentrations from the range from 0.001 to 10% by weight, based on the total weight of the formulation.

If vitamin A or vitamin A derivatives, or carotenes or derivatives thereof are the antioxidant(s), it is advantageous to choose their respective concentrations from the range from 0.001 to 10% by weight, based on the total weight of the formulation.

The active ingredients (one or more compounds) can also very advantageously be chosen according to the invention from the group of lipophilic active ingredients, in particular from the following group:

acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$ and vitamin $D_1$, but also bisabolol, unsaturated fatty acids, namely the essential fatty acids (often also called a vitamin F), in particular gamma-linolenic acid, oleic acid, eicosapentaenoic acid, docosahexaenoic acid and derivatives thereof, chloroamphenicol, caffeine, prostaglandins, thymol, camphor, extracts or other products of a vegetable and animal origin, e.g. evening primrose oil, borage oil or currant seed oil, fish oils, cod-liver oil and also ceramides and ceramide-like compounds, etc.

It is also advantageous to choose the active ingredients from the group of refatting substances, for example purcellin oil, Eucerit® and Neocerit®.

The active ingredient(s) is/are also particularly advantageously chosen from the group of NO synthase inhibitors, particularly if the preparations according to the invention are to be used for the treatment and prophylaxis of the symptoms of intrinsic and/or extrinsic skin ageing and for the treatment and prophylaxis of the harmful effects of ultraviolet radiation on the skin. A preferred NO synthase inhibitor is nitroarginine.

Accordingly, impregnated wipes for the purposes of the present invention are suitable particularly advantageously for the prophylaxis and treatment of cosmetic or dermatological skin changes, as occur e.g. during skin ageing. They are also advantageously suitable for the symptoms of dry or rough skin.

Skin ageing is caused e.g. by endogenous, genetically determined factors. As a result of ageing, the epidermis and dermis experience e.g. the following structural damage and functional disorders, which can also be covered by the term "senile xerosis":

a) dryness, roughness and formation of (dryness) wrinkles,
b) itching and
c) reduced refatting by sebaceous glands (e.g. after washing).

Exogenous factors, such as UV light and chemical noxae, can have a cumulative effect and, for example, accelerate or add to the endogenous ageing processes. The epidermis and dermis experience, in particular as a result of exogenous factors, e.g. the following structural damage and functional disorders in the skin, which go beyond the degree and quality of the damage in the case of chronological ageing:

d) visible vascular dilation (telangiectases, cuperosis);
e) flaccidity and formation of wrinkles;
f) local hyperpigmentation, hypopigmentation and abnormal pigmentation (e.g. age spots) and
g) increased susceptibility to mechanical stress (e.g. cracking).

In a particular embodiment, the present invention relates in particular to products for the care of skin aged naturally, and to the treatment of secondary damage of photoageing, in particular of the phenomena listed under a) to g).

The active ingredient(s) is/are also advantageously chosen from the group which includes catechins and bile esters of catechins and aqueous or organic extracts from plants or parts of plants which have a content of catechins or bile esters of catechins, such as, for example, the leaves of the Theaceae plant family, in particular of the species *Camellia sinensis* (green tea). Particularly advantageous are typical ingredients thereof (such as e.g. polyphenols or catechins, caffeine, vitamins, sugar, minerals, amino acids, lipids).

Catechins are a group of compounds which are to be regarded as hydrogenated flavones or anthocyanidines and are derivatives of "catechin" (catechol, 3,3',4',5,7-flavanpentol, 2-(3,4-dihydroxyphenyl)chroman-3,5,7-triol). Epicatechin ((2R,3R)-3,3',4',5,7-flavanpentol) is also an advantageous active ingredient for the purposes of the present invention.

Also advantageous are plant extracts with a content of catechins, in particular extracts of green tea, such as e.g. extracts from leaves of plants of the species *Camellia* spec., very particularly the types of tea *Camellia sinenis, C. assa-* mica, *C. taliensis* and *C. irrawadiensis* and hybrids of these with, for example, *Camellia japonica*.

Preferred active ingredients are also polyphenols or catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin and (−)-epigallocatechin gallate.

Flavone and its derivatives (also often collectively called "flavones") are also advantageous active ingredients for the purposes of the present invention. They are characterized by the following basic structure (substitution positions are shown):

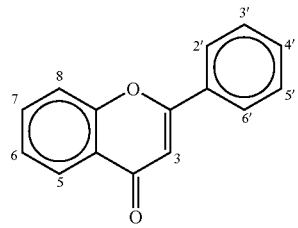

Some of the more important flavones which can also preferably be used in impregnation solutions according to the invention are given in the table below:

|  | OH substitution positions | | | | | | | |
| --- | --- | --- | --- | --- | --- | --- | --- | --- |
|  | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | − | + | − |
| Myricetin | + | + | + | − | − | + | + | + |

In nature, flavones are usually in glycosylated form.

According to the invention, the flavonoids are preferably chosen from the group of substances of the generic structural formula

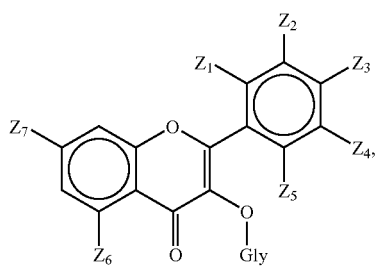

where $Z_1$ to $Z_7$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

According to the invention, the flavonoids can however, also advantageously be chosen from the group of substances of the generic structural formula

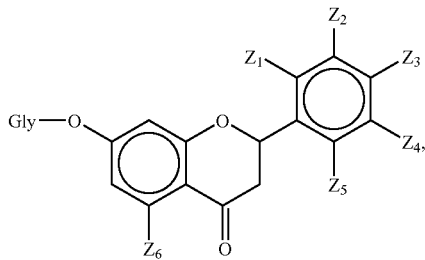

where $Z_1$ to $Z_6$, independently of one another, are chosen from the group consisting of H, OH, alkoxy and hydroxyalkoxy, where the alkoxy and hydroxyalkoxy groups may be branched or unbranched and have 1 to 18 carbon atoms, where Gly is chosen from the group mono and oligoglycoside radicals.

Preferably, such structures can be chosen from the group of substances of the generic structural formula

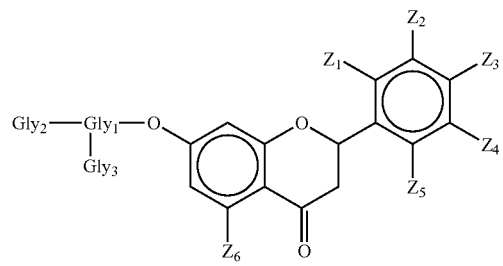

where $Gly_1$, $Gly_2$ and $Gly_3$, independently of one another, are monoglycoside radicals. $Gly_2$ and $Gly_3$ may also, individually or together, represent saturations by hydrogen atoms.

Preferably, $Gly_1$, $Gly_2$ and $Gly_3$, independently of one another, are chosen from the group of hexosyl radicals, in particular the rhamnosyl radicals and glucosyl radicals. However, hexosyl radicals, for example allosyl, altrosyl, galactosyl, gulosyl, idosyl, mannosyl and talosyl, can also be used advantageously in some circumstances. It may also be advantageous according to the invention to use pentosyl radicals.

$Z_1$ to $Z_5$ are, independently of one another, advantageously chosen from the group consisting of H, OH, methoxy, ethoxy and 2-hydroxyethoxy, and the flavone glycosides have the structure

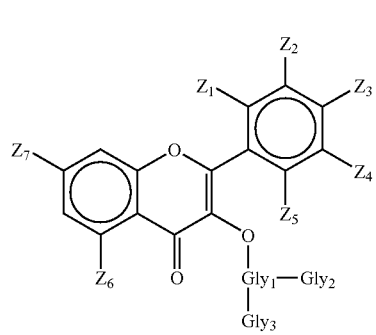

The flavone glycosides according to the invention are particularly advantageously chosen from the group given by the following structure:

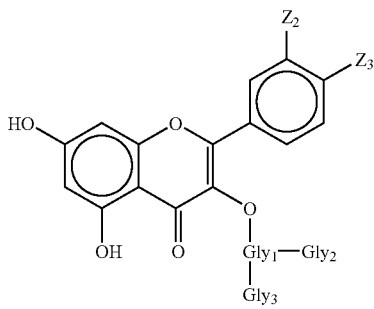

where $Gly_1$, $Gly_2$ and $Gly_3$, independently of one another, are monoglycoside radicals. $Gly_2$ and $Gly_3$ can also, individually or together, represent saturations by hydrogen atoms.

Preferably, $Gly_1$, $Gly_2$ and $Gly_3$, independently of one another, are chosen from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, can also advantageously be used in some circumstances. It may also be advantageous according to the invention to use pentosyl radicals.

For the purposes of the present invention, it is particularly advantageous to choose the flavone glucoside(s) from the group consisting of α-glucosylrutin, α-glucosylmyricetin, α-glucosylisoquercitrin, α-glucosylisoquercetin and α-glucosylquercitrin.

Particular preference is given according to the invention to α-glucosylrutin.

Also advantageous according to the invention are naringin (aurantin naringenin-7-rhamno-glucoside), hesperidin 3',5,7-trihydroxy-4'-methoxyflavanone-7-rutinoside, hesperidoside, hesperetin-7-O-rutinoside), rutin (3,3',4', 5,7-pentahydroxyflavone-3-rutinoside, quercetin-3-rutinoside, sophorin, birutan, rutabion, taurutin, phytomelin, melin), troxerutin (3,5-dihydroxy-3',4',7-tris(2-hydroxyethoxy)flavone-3-(6-O-(6-deoxy-α-L-mannopyranosyl)β-D-glucopyranoside)), monoxerutin (3,3',4',5-tetrahydroxy-7-(2-hydroxyethoxy)flavone-3-(6-O-(6-deoxy-α-L-mannopyranosyl)-β-D-glucopyranoside)), dihydrorobinetin (3,3',4',5',7-pentahydroxyflavanone), taxifolin (3,3',4',5,7-pentahydroxyflavanone), eriodictyol-7-glucoside (3',4', 5,7-tetrahydroxyflavanone-7 glucoside), flavanomarein (3',4',7,8-tetrahydroxyflavanone-7 glucoside) and isoquercetin (3,3',4',5,7-pentahydroxyflavanone-3-(β-D-glucopyranoside).

It is also advantageous to choose the active ingredient(s) from the group of ubiquinones and plastoquinones.

Ubiquinones are distinguished by the structural formula

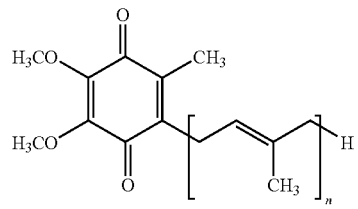

and are the most widespread and thus the most investigated bioquinones. Ubiquinones are referred to depending on the number of isoprene units linked in the side chain as Q-1, Q-2, Q-3 etc., or according to the number of carbon atoms, as U-5, U-10, U-15 etc. They preferably appear with certain chain lengths, e.g. in some microorganisms and yeasts where n=6. In most mammals including man, Q10 predominates.

Coenzyme Q10 is particularly advantageous and is characterized by the following structural formula:

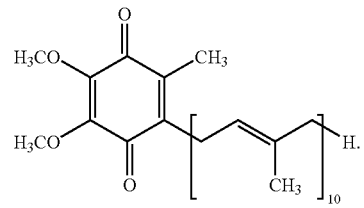

Plastoquinones have the general structural formula

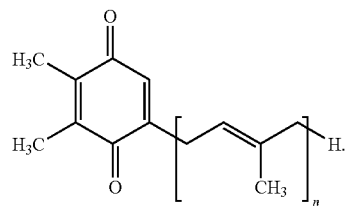

Plastoquinones differ in the number n of isoprene radicals and are referred to accordingly, e.g. PQ-9 (n=9). In addition, other plastoquinones with varying substituents on the quinone ring exist.

Creatine and/or creatine derivatives are preferred active ingredients for the purposes of the present invention. Creatine is characterized by the following structure:

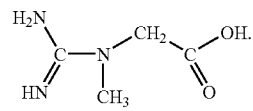

Preferred derivatives are creatine phosphate and creatine sulfate, creatine acetate, creatine ascorbate and the derivatives esterified at the carboxyl group with mono- or polyfunctional alcohols.

A further advantageous active ingredient is L-carnitine [3-hydroxy-4-(trimethylammonio)butyrobetaine]. Acylcarnitine chosen from the group of substances of the following general structural formula

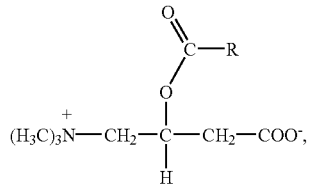

where R is chosen from the group of branched and unbranched alkyl radicals having up to 10 carbon atoms, are advantageous active ingredients for the purposes of the present invention. Preference is given to propionylcarnitine and, in particular, acetylcarnitine. Both enantiomers (D and L form) are to be used advantageously for the purposes of the present invention. It may also be advantageous to use any enantiomer mixtures, for example a racemate of D and L form.

Further advantageous active ingredients are sericoside, pyridoxol, vitamin K and biotin and aroma substances.

The list of said active ingredients and active ingredient combinations which can be used in the impregnation solutions according to the invention is, of course, not intended to be limiting. The active ingredients can be used individually or in any combinations with one another.

Cosmetic and dermatological wipes in the form of a sunscreen are favorable. It is, however, also advantageous for the purposes of the present invention to provide cosmetic and dermatological wipes whose main use purpose is not protection against sunlight, but which nevertheless contain a content of UV protection substances.

UV protection substances, like antioxidants, and, if desired, preservatives, also provide effective protection of the preparations themselves against spoilage.

Accordingly, for the purposes of the present invention, the impregnation solutions preferably additionally comprise at least one further UV-A and/or UV-B filter substance in addition to one or more UV filter substances according to the invention. The formulations may, although not necessarily, optionally also comprise one or more organic and/or inorganic pigments as UV filter substances which may be present in the water and/or oil phase.

Preferred inorganic pigments are metal oxides and/or other metal compounds which are insoluble or virtually insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides.

For the purposes of the present invention, such pigments may advantageously be surface-treated ("coated"), the intention being to form or retain, for example, an amphiphilic or hydrophobic character. This surface treatment can consist in providing the pigments with a thin hydrophobic layer by processes known per se.

Advantageous according to the invention are e.g. titanium dioxide pigments which have been coated with octylsilanol. Suitable titanium dioxide particles are available under the trade name T805 from Degussa. Also particularly advantageous are $TiO_2$ pigments coated with aluminum stearate, e.g. those available under the trade name MT 100 T from TAYCA.

A further advantageous coating of the inorganic pigments consists of dimethylpolysiloxane (also: dimethicone), a mixture of completely methylated, linear siloxane polymers which have been terminally blocked with trimethylsiloxy units. Particularly advantageous for the purposes of the present invention are zinc oxide pigments coated in this way.

Also advantageous is a coating of the inorganic pigments with a mixture of dimethylpolysiloxane, in particular dimethylpolysiloxane having an average chain length of from 200 to 350 dimethylsiloxane units, and silica gel, which is also referred to as simethicone. In particular, it is advantageous for the inorganic pigments to be additionally coated with aluminum hydroxide or aluminum oxide hydrate (also: alumina, CAS No.: 1333-84-2). Particularly advantageous are titanium dioxides which have been coated with simethicone and alumina, it also being possible for the coating to comprise water. An example thereof is the titanium dioxide available under the trade name Eusolex T2000 from Merck.

An advantageous organic pigment for the purposes of the present invention is 2,2'-methylenebis(6-(2H-benzotriazol-2-yl)-4-(1,1,3,3-tetramethylbutyl)phenol) [INCI: bisoctyltriazole], which is characterized by the chemical structural formula

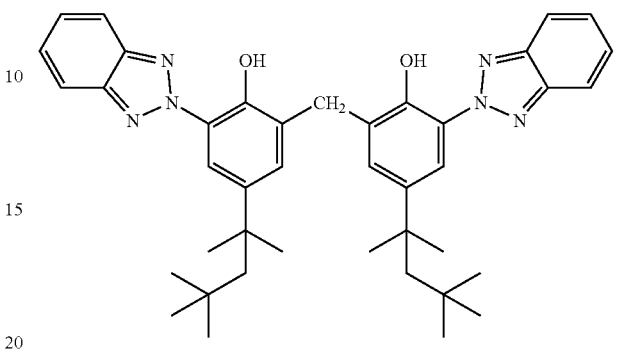

and is available under the trade name Tinosorb® M from CIBA-Chemikalien GmbH.

Impregnation solutions according to the invention advantageously comprise substances which absorb UV irradiation in the UV-A and/or UV-B region, the total amount of filter substances being, for example, 0.1% by weight to 30% by weight, preferably 0.5 to 20% by weight, in particular 1.0 to 15.0% by weight, based on the total weight of the preparations, in order to make available cosmetic impregnation solutions which protect the hair or the skin from the entire range of ultraviolet radiation. They can also be used as sunscreens for hair or skin.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the trade name Parsol® 1789 and by Merck under the trade name Eusolex® 9020.

Further advantageous UV-A filter substances are phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name bisimidazylates, which is available, for example, under the trade name Neo Heliopan AP from Haarmann & Reimer, and 1,4-di(2-oxo-10-sulfo-3-bornylidenemethyl)benzene and salts thereof (in particular the corresponding 10-sulfato compounds, in particular the corresponding sodium, potassium or triethanolammonium salt), which is also referred to as benzene-1,4-di(2-oxo-3-bornylidenemethyl-10-sulfonic acid).

Advantageous UV filter substances for the purposes of the present invention are also "broad-band filters", i.e. filter substances which absorb both UV-A and also UV-B radiation.

Advantageous broad-band filters or UV-B filter substances are, for example, bisresorcinyltriazine derivatives. Particularly preferred are 2,4-bis{[4-(2-ethylhexyloxy)-2hydroxy]phenyl}-6-(4-methoxyphenyl)-1,3,5-triazine (INCI: Aniso Triazine), which is available under the trade name Tinosorb® S from CIBA-Chemikalien GmbH, and 4,4', 4"-(1,3,5-triazine-2,4,6-triyltriimino)trisbenzoic acid tris(2-ethylhexyl ester), synonym: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

A particularly preferred UV filter substance for the purposes of the present invention is also an asymmetrically substituted s-triazine which is also referred to as dioctylbutylamidotriazone (INCI: dioctylbutamidotriazone) and is available under the trade name UVA-SORB HEB from Sigma 3V.

Also advantageous for the purposes of the present invention are 2,4-bis{[4-(3-sulfonato)2-hydroxypropyloxy)-2-hydroxy]phenyl}-6-(4methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyly)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

An advantageous broad-band filter for the purposes of the present invention is also 2-(2H-benzotriazol-2-yl)-4-methyl-6-[2-methyl-3-[1,3,3,3-tetramethy-1-[(trimethylsilyl)-oxy]disiloxanyl]propyl]phenol (CAS No.: 155633-54-8) with the INCI name Drometrizole trisiloxane.

The UV-B filters may be oil-soluble or water-soluble. Advantageous oil-soluble UV-B filter substances are e.g.:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino-(p-carbo-2'-ethyl-1'-hexyloxy)-1,3,5-triazine;

esters of benzalmalonic acid, preferably di(2-ethylhexyl) 4-methoxybenzalmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Advantageous water-soluble UV-B filter substances are e.g.:

salts of 2-phenylbenzimidazole-5-sulfonic acid, such as its sodium, potassium or its triethanolammonium salt, and the sulfonic acid itself;

sulfonic acid derivatives of 3-benzylidenecamphor, such as e.g. 4(2-oxo-3-bornylidenemethyl)benzenesulfonic acid, 2-methyl-5-(2-oxo-3-bornylidenemethyl)sulfonic acid and salts thereof.

A further light protection filter substance to be used advantageously according to the invention is ethylhexyl 2-cyano-3,3-diphenylacrylate (octocrylene), which is available from BASF under the trade name Uvinul® N 539.

It may also be of considerable advantage to use polymer-bonded or polymeric UV filter substances in impregnation solutions according to the present invention, particularly those described in WO-A-92/20690.

In some instances, it may also be advantageous to incorporate further UV-A and/or UV-B filters according to the invention into the cosmetic or dermatological impregnation solutions, for example certain salicylic acid derivatives, such as 4-isopropylbenzyl salicylate, 2-ethylhexyl salicylate (=octyl salicylate), homomenthyl salicylate.

The list of said UV filters which can be used for the purposes of the present invention is not of course intended to be limiting.

The cosmetic and dermatological wipes according to the invention can also advantageously comprise dyes and/or color pigments, particularly if they are to be used in the decorative cosmetics sector. The dyes and pigments can be chosen from the corresponding positive list of the Cosmetics Directive or the EC list of cosmetic colorants. In most cases they are identical to the dyes approved for foods. Advantageous color pigments are, for example, titanium dioxide, mica, iron oxides (e.g. $Fe_2O_3$, $Fe_3O_4$, FeO(OH)) and/or zinc oxide. Advantageous dyes are, for example, carmine, Berlin blue, chrome oxide green, ultramarine blue and/or manganese violet. It is particularly advantageous to choose the dyes and/or color pigments from the following list. The Colour Index Numbers (CIN) are taken from the *Rowe Colour Index, 3rd Edition, Society of Dyers and Colourists*, Bradford, England, 1971.

| Chemical or other name | CIN | Color |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydroxy-naphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthyl-carboxylic acid | 15850 | red |
| 1-(2-Sulfo-4-methyl-5-chloro-1-phenylazo)-2-hydroxy-naphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |

| Chemical or other name | CIN | Color |
|---|---|---|
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2",4"-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4"-(4"-Sulfo-1"-phenylazo)-7'-sulfo-1'-naphthylazo]-1-hydroxy-7-aminonaphthalene-3,6-disulfonic acid | 27755 | black |
| 4'-[(4"-Sulfo-1"-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotinaldehyde ($C_{30}$) | 40820 | orange |
| trans-Apo-8'-carotinic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4"-bis(diethylamino)tri-phenylcarbinol | 42051 | blue |
| 4-[(4-N-Ethyl-p-sulfobenzylamino)phenyl(4-hydroxy-2-sulfophenyl)(methylene)-1-(N-ethyl-N-p-sulfobenzyl)-2,5-cyclohexadienimine] | 42053 | green |
| Acid Blue 7 | 42080 | blue |
| (N-Ethyl-p-sulfobenzylamino)phenyl(2-sulfophenyl)-methylene-(N-ethyl-N-p-sulfobenzyl)$\Delta^{2,5}$-cyclohexadienimine | 42090 | blue |
| Acid Green 9 | 42100 | green |
| Diethyldisulfobenzyldi-4-amino-2-chloro-di-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4"-(N-diethyl)amino-2-methyl-N-ethyl-N-m-sulfobenzylfuchsonimmonium | 42735 | blue |
| 4'-(N-Dimethyl)amino-4"-(N-phenyl)aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methyl-4'-sulfophenylamino)-9-(2"-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6, 19; Natural Red 1 | 75100 | yellow |
| Bixin, Norbixin | 75120 | orange |
| Lycopene | 75125 | yellow |
| trans-alpha-, beta-and gamma-carotene | 75130 | orange |
| Keto-and/or hydroxyl derivates of carotene | 75135 | yellow |
| Guanine or pearlizing agent | 75170 | white |
| 1,7-Bis(4-hydroxy-3-methoxyphenyl)1,6-heptadiene-3,5-dione | 75300 | yellow |
| Complex salt (Na, Al, Ca) of carminic acid | 75470 | red |
| Chlorophyll a and b; copper compounds of chlorophylls and Chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 ad 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment black 9 | 77267 | black |
| Carbo medicinalis vegetabilis | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide, hydrated | 77492 | yellow |
| Iron oxide | 77499 | black |
| Mixtures of iron (II) and iron (III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7 H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar colouring | | brown |
| Capsanthin, capsorubin | | orange |
| Betanin | | red |
| Benzopyrylium salts, Anthocyans | | red |
| Aluminum, zinc, magnesium and calcium stearate | | white |
| Bromothymol blue | | blue |
| Bromocresol green | | green |
| Acid Red 195 | | red |

If the wipes according to the invention are intended for use in the facial area, it is favorable to choose one or more substances from the following group as the dye: 2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalone disulfonic acid, aluminum salt of indigo disulfonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are impregnated wipes with a content of pearlescent pigments. Preference is given in particular to the types of pearlescent pigments listed below:
1. Natural pearlescent pigments, such as, for example
   "pearl essence" (guanine/hypoxanthin mixed crystals from fish scales) and
   "mother of pearl" (ground mussel shells)
2. Monocrystalline pearlescent pigments, such as, for example, bismuth oxychloride (BiOCl)
3. Layer substrate pigments: e.g. mica/metal oxide Bases for pearlescent pigments are, for example, pulverulent pigments or castor oil dispersions of bismuth oxychloride and/or titanium dioxide, and bismuth oxichloride and/or titanium dioxide on mica. The luster pigment listed under CIN 77163, for example, is particularly advantageous.

Also advantageous are, for example, the following types of pearlescent pigment based on mica/metal oxide:

| Group | Coating/layer thickness | Color |
|---|---|---|
| Silver-white pearlescent pigments | $TiO_2$: 40-60 nm | silver |
| Interference pigments | $TiO_2$: 60-80 nm | yellow |
|  | $TiO_2$: 80-100 nm | red |
|  | $TiO_2$: 100-140 nm | blue |
|  | $TiO_2$: 120-160 nm | green |
| Color luster pigments | $Fe_2O_3$ | bronze |
|  | $Fe_2O_3$ | copper |
|  | $Fe_2O_3$ | Red |
|  | $Fe_2O_3$ | Red-violet |
|  | $Fe_2O_3$ | Red-green |
|  | $Fe_2O_3$ | Black |
| Combination pigments | $TiO_2/Fe_2O_3$ | Gold shades |
|  | $TiO_2/Cr_2O_3$ | Green |
|  | $TiO_2$/Berlin blue | deep blue |
|  | $TiO_2$/carmine | red |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("ronaspheres"), which are marketed by Merck and are particularly suitable for the optical reduction of fine lines.

It can moreover be advantageous to dispense completely with a substrate such as mica. Particular preference is given to iron pearlescent pigments prepared without the use of mica. Such pigments are obtainable, for example, under the trade name Sicopearl Kupfer 1000 from BASF.

In addition, also particularly advantageous are effect pigments which are available under the trade name Metasome Standard/Glitter in various colors (yellow, red, green, blue) from Flora Tech. The glitter particles are present here in the mixtures with various auxiliaries and dyes (such as, for example, the dyes with the Colour Index (CI) Numbers 19140, 77007, 77289, 77491).

The dyes and pigments may be present either individually or in a mixture, and can be mutually coated with one another, different coating thicknesses generally giving rise to different color effects. The total amount of dyes and color-imparting pigments is advantageously chosen from the range from e.g. 0.1% by weight to 30% by weight, preferably from 0.5 to 15% by weight, in particular from 1.0 to 10% by weight, in each case based on the total weight of the impregnation solutions.

Also advantageous for the purposes of the present invention are wipes which are used as cosmetic or dermatological deodorant or antiperspirant wipes.

According to the invention, the wipes particularly advantageously comprise one or more of the customary deodorizing and/or antiperspirant active ingredients, for example odor maskers, such as the customary perfume constituents, odor absorbers, for example the phyllosilicates described in the patent laid-open specifiation DE-P 40 09 347, and of these in particular montmorillonite, kaolinite, nontronite, saponite, hectorite, bentonite, smectite, and furthermore, for example, zinc salts of ricinoleic acid. Germicidal agents are also suitable for incorporation into the preparations according to the invention. Advantageous substances are 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in the patent laid-open specifications DE-37 40 186, DE-39 38 140, DE-42 04 321, DE-42 29 707, DE-42 29 737, DE-42 37 081, DE-43 09 372, DE-43 24 219.

The customary antiperspirant active ingredients can likewise advantageously be used, for example, aluminum chloride, aluminum chlorhydrate, nitrate, sulfate, acetate etc. In addition, also advantageous are zinc, magnesium and zirconium compounds. Customary antiperspirant active ingredients which can preferably be used are, for example, described in: H. P. Fiedler, Der Schweiß, Editio Cantor, Aulendorf, 2nd Edition, pp. 303-377, Chapter K: "*Mittel zur Hemmung der Transpiration*" [Agents for inhibiting perspiration].

It is also advantageous for the purposes of the present invention to provide cosmetic and dermatological wipes whose main purpose is not the deodorizing or antiperspirant action, but which nevertheless have a content of customary deodorizing and/or antiperspirant active ingredients.

The wipes according to the invention are also highly suitable as carriers for dermatological active ingredients, e.g. as carriers for substances effective against acne. Acne is a skin disorder with many forms and causes, characterized by non-inflamed and inflamed bumps, originating from blocked hair follicles (comedones) which can lead to the formation of pustules, abscesses and scars. The most frequent is Acne vulgaris which occurs predominantly in puberty. Causative conditions for Acne vulgaris are the keratinization and blocking of the hair follicle opening, the production of sebum, which is dependent on the level of male sex hormones in the blood, and the production of free fatty acids and tissue-damaging enzymes by bacteria (*propionibacterium acnes*).

It is therefore advantageous to add to the impregnation solutions according to the invention substances which are effective against acne, which are effective, for example, against *propionibacterium acnes* (for example those described in DE-A 42 29 707, DE-A 43 05 069, DE-A 43 07 976, DE-A 43 37 711, DE-A 43 29 379), but also other substances effective against acne, for example all-trans-retinoic acid, 13-cis-retinoic acid and related substances) or antiinflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol, and antibiotics and/or keratolytics. Keratolytics are substances which soften keratinized skin (such as, for example, warts, corns, calouses and the like) so that it can be removed more easily or so that it falls off or peels off.

All common substances effective against acne can be used advantageously, in particular benzoyl peroxide, bituminosulfonates (ammonium, sodium and calcium salts of shale oil sulfonic acids), salicylic acid (2-hydroxybenzoic acid), miconazole (1-[2-(2,4-dichlorobenzyloxy)-2-(2,4-dichlorophenyl)ethyl]imidazole) and derivatives, adapalene (6-[3-(1-adamantyl)-4-methoxyphenyl]-2-naphthoic acid), azaleic acid (nonanedioc acid), mesulfene (2,7-dimethylthianthrene, $C_{14}H_{12}S_2$), and aluminum oxide, zinc oxide and/or finely divided sulfur.

The amount of antiacne agents (one or more compounds) in the impregnation solutions is preferably 0.01 to 30% by weight, particularly preferably 0.1 to 20% by weight, in particular 1 to 10% by weight, based on the total weight of the impregnation solution.

According to the invention, wipes are used in combination with the low-viscosity cosmetic and dermatological impregnation solutions, which wipes consist of, in particular, water-jet-consolidated and/or water-jet-impressed nonwoven (spunlaced material).

The macroimpression introduced into the nonwoven can have any desired pattern. The choice to be made depends, firstly, on the impregnation to be applied and, secondly, on the later intended use for the wipe.

Large cavities on the nonwoven surface and within the nonwoven facilitate the uptake of soiling and contaminations when the impregnated wipe is passed over the skin. The cleaning action is increased many times over relative to the unimpregnated wipes.

The thickness of the nonwoven is advantageously approximately twice as large as the unimpregnated nonwoven as a result of elevations produced by the impression. In preferred embodiments, the impressed nonwoven is between 5% and 50%, very particularly preferably between 10% and 25%, thicker than the unimpressed material.

Furthermore, the impressed nonwoven has particular properties which permit the use as carrier material for emulsions or other preparations.

For example, the tear strength is, in particular [N/50 mm]

| | | |
|---|---|---|
| In the dry state | Machine direction | >60, preferably >80 |
| | Cross direction | >20, preferably >30 |
| In the impregnated state | Machine direction | >4, preferably >60 |
| | Cross direction | >10, preferably >20 |

-continued

The expandability of the wipe is preferably

| | | |
|---|---|---|
| In the dry state | Machine direction | 15% to 100%, preferably 20% and 50% |
| | Cross direction | 40% to 120%, preferably 50% and 85% |
| In the impregnated state | Machine direction | 15% to 100%, preferably 20% and 40% |
| | Cross direction | 40% to 120%, preferably 50% and 85% |

It has proven advantageous for the wipe to have a weight of 35 to 120 g/m², preferably from 40 to 60 g/m² (measured at 20° C.±2° C. and at a humidity of the room air of 65%±5% for 24 hours).

The thickness of the nonwoven is preferably 0.4 mm to 1.5 mm, in particular 0.6 mm to 0.9 mm.

Finally, it is particularly advantageous for the wipe to have a "surface linting" of less than 4 mg/1000 mm², preferably less than 2 mg/1000 mm².

Starting materials for the nonwoven material of the wipe which can be used are generally all organic and inorganic natural and synthetic based fiber materials. Examples which may be given are viscose, cotton, jute, hemp, sisal, silk, wool, polypropylene, polyester, polyethylene terephthalate (PET), aramid, nylon, polyvinyl derivatives, polyurethanes, polylactide, polyhydroxyalkanoate, cellulose esters and/or polyethylene and also mineral fibers, such as glass fibers or carbon fibers. However, the present invention is not limited to said materials, it being possible to use a large number of further fibers for forming the nonwoven.

In a particularly advantageous embodiment of the nonwoven, the fibers consist of a mixture of 70% of viscose and 30% of PET.

Also particularly advantageous are fibers of high-strength polymers, such as polyamide, polyesters and/or highly drawn polyethylene.

Moreover, the fibers can also be colored in order to be able to emphasize and/or increase the optical attractiveness of the nonwoven. The fibers may additionally comprise UV stabilizers and/or preservatives.

The fibers used to form the wipe preferably have a water-absorption rate of more than 60 mm/[10 min] (measured using the EDANA Test 10.1-72), in particular more than 80 mm/[10 min].

The fibers used to form the wipe then preferably have a water-absorption capacity of more than 5 g/g (measured using the EDANA Test 10.1-72), in particular more than 8 g/g.

The examples below serve to illustrate the impregnation solutions according to the invention without limiting them. The numerical values in the examples are percentages by weight, based on the total weight of the respective preparations.

EXAMPLES

Example 1

| Constituent | Amount/% by weight |
|---|---|
| Paraffinum liquidum | 99.8 |
| Perfume | 0.2 |

Example 2

Microemulsion

| Constituent | Amount/% by weight |
|---|---|
| Water | 82.0 |
| Paraffinum liquidum | 8.0 |
| Glycerol | 5.0 |
| Octyl stearate | 2.0 |
| Glyceryl Stearate, Ceteareth-20, Ceteareth-12, Cetearyl Alcohol, Cetyl Palmitate | 1.5 |
| Phenoxyethanol, Methylparaben, Ethyl-Paraben, Propylparaben, Butylparaben, Isobutylparaben | 0.5 |
| Perfume | 0.4 |
| Ceteareth-20 | 0.3 |
| Methylparaben | 0.3 |
| Total: | 100.0 |

Example 3

Microemulsion

| Constituent | Amount/% by weight |
|---|---|
| Water | 75.0 |
| Paraffinum liquidum | 0.5 |
| Glycerol | 7.0 |
| Octyl stearate | 1.0 |
| Glyceryl stearate, Ceteareth-20, Ceteareth-12, Cetearyl alcohol, Cetyl palmitate | 3.0 |
| Phenoxyethanol, Methylparaben, Ethyl-paraben, Propylparaben, Butylparaben, Isobutylparaben | 0.5 |
| Perfume | 2.0 |
| Ceteareth-20 | 10.0 |
| Methylparaben | 1.0 |
| Total: | 100.0 |

Example 4

Aqueous Impregnation Solution

| Constituent | Amount/% by weight |
|---|---|
| Water | 96.89 |
| Butylene glycol | 1.0 |
| PEG-40 hydrogenated castor oil | 0.8 |
| Phenoxyethanol, Methylparaben, Ethyl-paraben, Propylparaben, Butylparaben, Isobutylparaben | 0.65 |
| Potassium sorbate | 0.3 |
| Perfume | 0.2 |
| Citric acid | 0.16 |
| Total: | 100.0 |

Example 5

Aqueous Impregnation Solution

| Constituent | Amount/% by weight |
|---|---|
| Water | 95.0 |
| Butylene glycol | 1.0 |
| PEG-40 hydrogenated castor oil | 1.0 |
| Phenoxyethanol, Methylparaben, Ethyl-paraben, Propylparaben, Butylparaben, Isobutylparaben | 1.5 |
| Potassium sorbate | 0.5 |
| Perfume | 0.5 |
| Citric acid | 0.5 |
| Total: | 100.0 |

Example 6

| Constituent | Amount/% by weight |
|---|---|
| Cyclomethicone | 65.5 |
| Dimethicone | 20.0 |
| Silicone gum | 7.0 |
| Phenyltrimethicone | 7.0 |
| Perfume | 0.5 |
| Total: | 100.0 |

Example 7

Alcoholic Impregnation Solution

| Constituent | Amount/% by weight |
|---|---|
| Ethanol | 60.0 |
| Water | 34.5 |
| Glycerol | 5.0 |
| Perfume | 0.5 |
| Total: | 100.0 |

Example 8

Alcoholic Impregnation Solution

| Constituent | Amount/% by weight |
|---|---|
| Ethanol | 60.0 |
| Water | 24.0 |
| Glycerol | 5.0 |
| Isopropyl alcohol | 5.0 |
| Ethylenediamine | 1.0 |
| Dexpanthenol | 1.0 |

-continued

| Constituent | Amount/% by weight |
|---|---|
| Carbomer | 3.0 |
| Perfume | 0.5 |
| Dye | 0.5 |
| Total: | 100.0 |

Example 9

Aftersun/skincare Microemulsion

| Constituent | Amount/% by weight |
|---|---|
| Ceteth-15 | 6 |
| Glyceryl isostearate | 2 |
| Cetyl alcohol | 1 |
| Dicaprylyl carbonate | 5 |
| Octyldodecanol | 3 |
| Cylomethicone | 1 |
| Butylene glycol | 3 |
| Ethanol | 5 |
| DMDM hydantoin | 0.6 |
| Octoxyglycerol | 1 |
| Antioxidants | 0.5 |
| Perfume | 0.5 |
| Dyes | 0.3 |
| Water | ad 100 |

Example 10

Nongreasy Bodycare Emulsion

| Constituent | % by weight |
|---|---|
| Ceteareth-12 | 6 |
| Glyceryl stearate | 3.5 |
| Cetyl palmitate | 3 |
| Dicaprylyl ether | 5 |
| Cyclomethicone | 3 |
| Phenyltrimethicone | 1 |
| Paraffin wax | 2 |
| Glycerol | 7.5 |
| Parabens | 1 |
| Phenoxyethanol | 1 |
| AGR | 0.5 |
| Perfume | 0.5 |
| Dyes | 0.5 |
| Water | ad 100 |

Example 11

Sunscreen for a Silky Feel on the Skin

| Constituent | % by weight |
|---|---|
| Ceteareth-20 | 5.5 |
| Glyceryl stearate | 4 |
| Stearyl alcohol | 3 |
| Dicaprylyl ether | 5 |

-continued

| Constituent | % by weight |
|---|---|
| Octyldodecanol | 3 |
| Phenyltrimethicone | 1 |
| Bisethylhexyloxyphenol methoxyphenyl triazine | 2 |
| Octocrylene | 7 |
| Diethylhexyl butamidotriazone | 1 |
| Ethylhexyl methoxycinnamate | 4 |
| Butylene glycol | 1 |
| Vitamin E acetate | 1 |
| PVP/hexadecene copolymer | 1 |
| Parabens | 1 |
| Antioxodants | 0.5 |
| Perfume | 0.5 |
| Water | ad 100 |

Example 12

Sunscreen Formulation

| Constituent | % by weight |
|---|---|
| Ceteareth-20 | 6.5 |
| Glyceryl stearate | 2 |
| Stearyl alcohol | 1 |
| Dicaprylyl carbonate | 5 |
| Octyldodecanol | 3 |
| C12–15 alkyl benzoates | 1 |
| Titanium dioxide | 2 |
| Bisethylhexyloxyphenol methoxyphenyl triazine | 2 |
| Octocrylene | 7 |
| Ethylhexyl methoxycinnamate | 4 |
| Parabens | 1 |
| Antioxidants | 0.5 |
| Perfume | 0.5 |
| Water | ad 100 |

Example 13

Sonnenschutzformulierung

| Constituent | % by weight |
|---|---|
| Steareth-20 | 6.5 |
| Glyceryl isostearate | 2 |
| Cetyl alcohol | 1 |
| Dicaprylyl carbonate | 5 |
| Shea butter | 3 |
| C12–15 alkyl benzoates | 1 |
| Bisethylhexyloxyphenol methoxyphenyl triazine | 2 |
| Butylmethoxydibenzoylmethane | 1 |
| Ethylhexyl triazone | 2 |
| Phenylbenzimidazole sulfonic acid | 2 |
| Ethylhexyl methoxycinnamate | 4 |
| Glycerol | 10 |
| Tricontanyl PVP | 1 |
| Citrate buffer | 1 |
| Parabens | 1 |
| Antioxidants | 0.5 |
| Perfume | 0.5 |
| Water | ad 100 |

Example 14

Sunscreen Formulation

| Constituent | % by weight |
| --- | --- |
| Ceteareth-30 | 7 |
| Glyceryl isostearate | 2.5 |
| Cetyl alcohol | 1 |
| Dicaprylyl carbonate | 4 |
| Capric/caprylic triglyceride | 2 |
| C12–15 alkyl benzoates | 6 |
| Methylene bisbenzotriazolyl tetramethylbutylphenol | 2 |
| Butyl methoxydibenzoylmethane | 2 |
| Ethylhexyl triazone | 4 |
| Bisimidazylate | 2 |
| Methylbenzylidene camphor | 4 |
| Glycerol | 5 |
| PVP hexadecene copolymer | 1 |
| Parabens | 1 |
| Antioxidants | 0.5 |
| Perfume | 0.5 |
| Water | ad 100 |

Example 15

Sunscreen Formulation

| Constituent | % by weight |
| --- | --- |
| Ceteareth-20 | 7.5 |
| Glyceryl stearate | 3 |
| Cetyl palmitate | 1.5 |
| Dicaprylyl carbonate | 5 |
| Cocoglycerides | 2 |
| C12–15 alkyl benzoates | 6 |
| Barium sulfate | 2 |
| Bisethylhexyloxyphenol methoxyphenyl triazine | 2 |
| Ethylhexyl triazone | 4 |
| Bisimidazylate | 1 |
| Phenylbenzimidazole sulfonic acid | 2 |
| Methylbenzylidene camphor | 4 |
| PVP hexadecene copolymer | 1 |
| NaOH | 0.5 |
| Parabens | 1 |
| Antioxidants | 0.5 |
| Perfume | 0.5 |
| Water | ad 100 |

Example 16

Aftersun/skincare Formulation

| Constituent | % by weight |
| --- | --- |
| Ceteth-15 | 6 |
| Glyceryl isostearate | 2 |
| Cetyl alcohol | 1 |
| Dicaprylyl carbonate | 5 |
| Shea butter | 1 |
| Octyldodecanol | 3 |
| Cyclomethicone | 1 |
| Mineral oil | 2 |
| Ethanol | 5 |
| Parabens | 1 |
| Antioxidants | 0.5 |
| Perfume | 0.5 |
| Water | ad 100 |

Oil - Examples

Oil-1

| Constituent | % by weight |
| --- | --- |
| Capric/caprylicic triglyceride | 2 |
| C12–15 alkyl benzoates | 6 |
| Butyl methoxydibenzoylmethane | 2 |
| Ethylhexyl triazone | 2 |
| Bisethylhexyloxyphenol methoxyphenyl triazine | 1 |
| Methylbenzylidene camphor | 4 |
| Shea butter | 1 |
| Butylene glycol dicaprate/dicaprylate | 3 |
| Dimethicone | 5 |
| Parabens | 1 |
| Antioxidants | 0.5 |
| Perfume | 0.5 |
| Mineral oil | ad 100 |

Oil-2

| Constituent | % by weight |
| --- | --- |
| Dicaprylyl carbonate | 5 |
| Bisethylhexyloxyphenol methoxyphenyl triazine | 2 |
| Ethylhexyl triazone | 4 |
| Methylbenzylidene camphor | 4 |
| Shea butter | 1 |
| Octyl dodecanol | 3 |
| Cyclomethicone | 1 |
| Vitamin E | 1 |
| Perfume | 0.5 |
| Mineral oil | ad 100 |

Oil-3

| Constituent | % by weight |
| --- | --- |
| Dicaprylyl carbonate | 5 |
| Bisethylhexyloxyphenol methoxyphenyl triazine | 2 |
| Diethylhexyl butamido triazone | 4 |
| Methylbenzylidene camphor | 1 |
| Shea butter | 1 |
| Phenyltrimethicone | 1 |
| Vitamin E | 2 |
| Perfume | 0.5 |
| Cyclomethicone | ad 100 |

Oil-4

| Constituent | % by weight |
| --- | --- |
| Ethylhexyl methoxycinnamate | 10 |
| Dicaprylyl carbonate | 5 |
| Bisethylhexyloxyphenol methoxyphenyl triazine | 2 |
| Diethylhexyl butamidotriazone | 4 |
| Octocrylene | 5 |
| Shea butter | 1 |
| Phenyltrimethicone | 1 |
| Vitamin E | 1 |
| Perfume | 1 |
| Cyclomethicone | ad 100 |

Aqueous formulation:

| Constituent | % by weight |
| --- | --- |
| Bisimidazylate | 1 |
| Phenylbenzimidazolesulfonic acid | 2 |
| Glycerol | 10 |
| Parabens | 1 |
| Antioxidants | 0.5 |
| Perfume | 0.5 |
| Water | ad 100 |

The invention claimed is:

1. A cosmetic or dermatological wipe, wherein the wipe consist of a water-jet consolidated and water-jet impressed nonwoven material which is moistened with a cosmetic or dermatological impregnation liquid which comprises at least one of oil, a silicone oil and a lipophilic substance and has a water content of less than 0.5% by weight, based on a total weight of the impregnation liquid, a viscosity of less than 2,000 mPa·s and wherein the wipe exhibits a uniform sequence of elevations and indentations in the nonwoven material.

2. The wipe of claim 1, wherein the impregnation liquid is alcohol-based.

3. The wipe of claim 1, wherein the impregnation liquid is free of oil.

4. The wipe of claim 1, wherein the impregnation liquid comprises a moisturizer.

5. The wipe of claim 1, wherein the impregnation liquid comprises a UV filter.

6. The wipe of claim 1, wherein the impregnation liquid comprises a perfume.

7. The wipe of claim 1, wherein the impregnation liquid comprises an antioxidant.

8. The wipe of claim 1, wherein the impregnation liquid comprises an emulsion.

9. The wipe of claim 1, wherein the impregnation liquid comprises a microemulsion.

10. The wipe of claim 1, wherein a weight ratio of the nonwoven material to the impregnation liquid is from 1:1 to 1:5.

11. The wipe of claim 1, wherein the nonwoven material is from 5% to 50% thicker than an identical nonwoven material which has not been water-jet impressed.

12. The wipe of claim 11, wherein the nonwoven material is from 10% to 25% thicker than an identical nonwoven material which has not been water-jet impressed.

13. The wipe of claim 1, wherein the nonwoven material comprises fibers of at least one of viscose, cotton, jute, hemp, sisal, silk, wool, polypropylene, polyethylene, polyester, aramid, nylon, polyurethane, polylactide, polyhydroxyalkanoate and cellulose ester.

14. The wipe of claim 13, wherein the nonwoven material comprises fibers of viscose and polyethylene terephthalate.

15. The wipe of claim 1, wherein the moistened wipe exhibits at least one of (a) a tear strength in machine direction of greater than 60 N/50 mm and a tear strength in cross direction of greater than 20 N/50 mm and (b) an expandability in machine direction of from 20% to 40% and an expandability in cross direction of from 50% to 85%.

16. A cosmetic or dermatological wipe, wherein the wipe consists a water-jet consolidated and of a water-jet impressed nonwoven material which is moistened with a cosmetic or dermatological impregnation liquid having a viscosity of less than 2,000 mPa·s and comprises at least one of oil, a silicone oil and a lipophilic substance and has a water content of less than 0.5% by weight, based on a total weight of the impregnation liquid and wherein the wipe exhibits a uniform sequence of elevations and indentations in the nonwoven material, the impregnation liquid being an emulsion which comprises at least one of a moisturizer, a wax, a UV filter, a pigment, a perfume, an antioxidant, a plant extract, a deodorant or antiperspirant active ingredient and a dermatological active ingredient.

17. A cosmetic or dermatological wipe, wherein the wipe consists of a water-jet consolidated and water-jet impressed nonwoven material which is moistened with a cosmetic or dermatological impregnation liquid having a viscosity of less than 2,000 mPa·s and comprises at least one of oil, a silicone oil and a lipophilic substance and has a water content of less than 0.5% by weight, based on a total weight of the impregnation liquid and wherein the wipe exhibits a uniform sequence of elevations and indentations in the nonwoven material, a weight ratio of the nonwoven material to the impregnation liquid being not higher than 1:1 and the impregnation liquid comprising a microemulsion.

18. The wipe of claim 17, wherein the moistened wipe exhibits a tear strength in machine direction of greater than 60 N/50 mm, a tear strength in cross direction of greater than 20 N/50 mm, an expandability in machine direction of from 20% to 40% and an expandability in cross direction of from 50% to 85%.

* * * * *